United States Patent [19]

Walsh et al.

[11] Patent Number: 4,657,019

[45] Date of Patent: Apr. 14, 1987

[54] ANASTOMOSIS DEVICES AND KITS

[75] Inventors: David J. Walsh, Mississauga; William M. Lougheed, Toronto; Fred Gentili, Toronto; Mahmood Fazl, Toronto, all of Canada

[73] Assignee: Idea Research Investment Fund, Inc., Toronto, Canada

[21] Appl. No.: 598,900

[22] Filed: Apr. 10, 1984

[51] Int. Cl.⁴ .............................................. A61B 17/11
[52] U.S. Cl. ............................ 128/334 C; 128/334 R; 128/354
[58] Field of Search ............... 128/334 C, 334 R, 340, 128/321, 354, 325

[56] References Cited

U.S. PATENT DOCUMENTS

| | | | |
|---|---|---|---|
| 2,453,056 | 11/1948 | Zack | 128/334 C |
| 3,032,039 | 5/1962 | Beaty | 128/326 |
| 3,155,095 | 11/1964 | Brown | 128/334 C |
| 3,683,926 | 8/1972 | Suzuki | 128/334 R |
| 4,366,819 | 1/1983 | Kaster | 128/334 C |

FOREIGN PATENT DOCUMENTS 1181563 2/1970 United Kingdom ............ 128/334 C

Primary Examiner—Michael H. Thaler
Attorney, Agent, or Firm—Bachman & LaPointe

[57] ABSTRACT

Devices, kits and methods for non-suture end-to-end and end-to-side anastomosis of tubular tissue members employ tubular connection members having clip retaining elements comprising annular grooves or flanges in the connection members; and spring clips which comprise a ring-shaped body with separable opposed ends whereby a circular opening defined by the body can be enlarged; the opposed ends have handling elements to facilitate handling of the clips and separation of the opposed ends; specially developed instruments facilitate use of the devices and the anastomosis procedure can be completed much more rapidly than with conventional techniques and has the significant advantage of intima to intima contact at the site of anastomosis with no foreign material exposed to the lumen of the vessels being joined.

5 Claims, 43 Drawing Figures

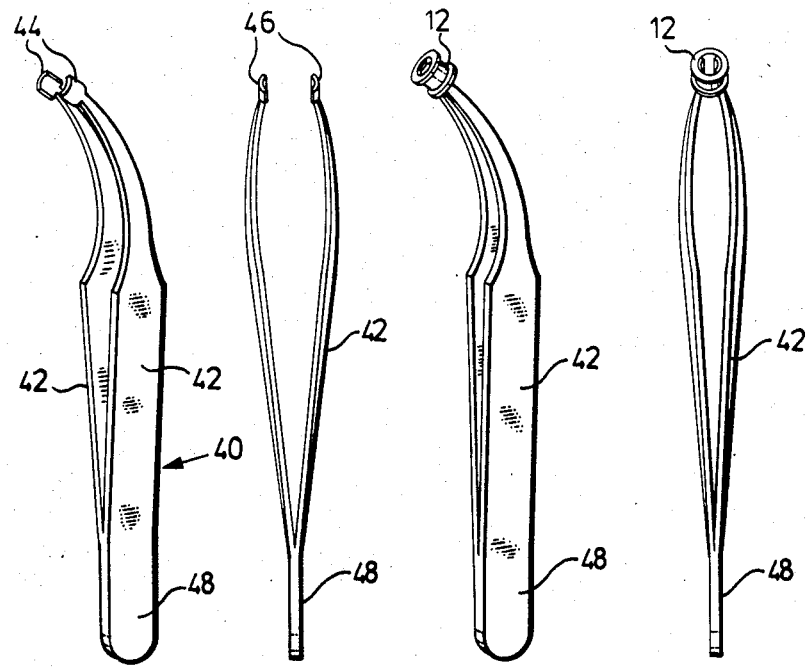
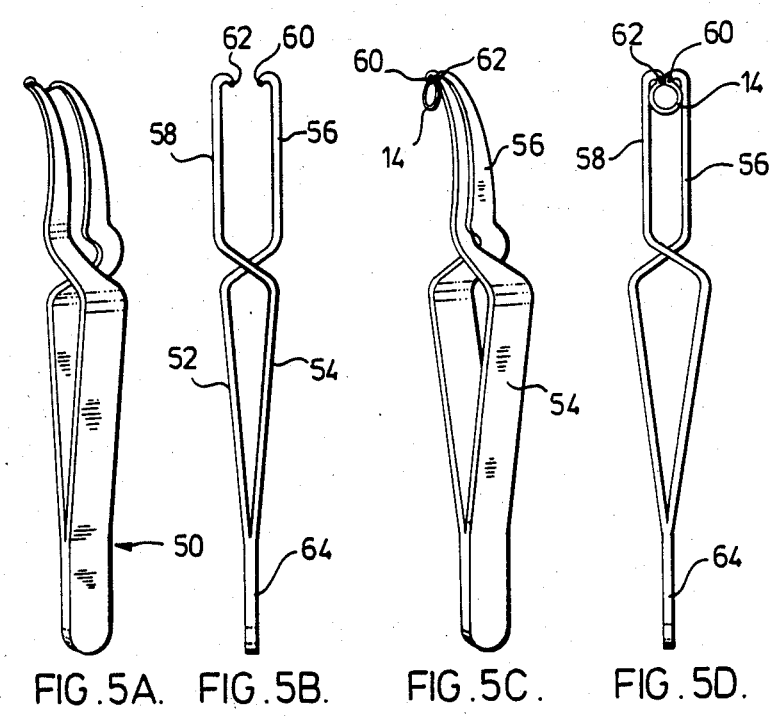

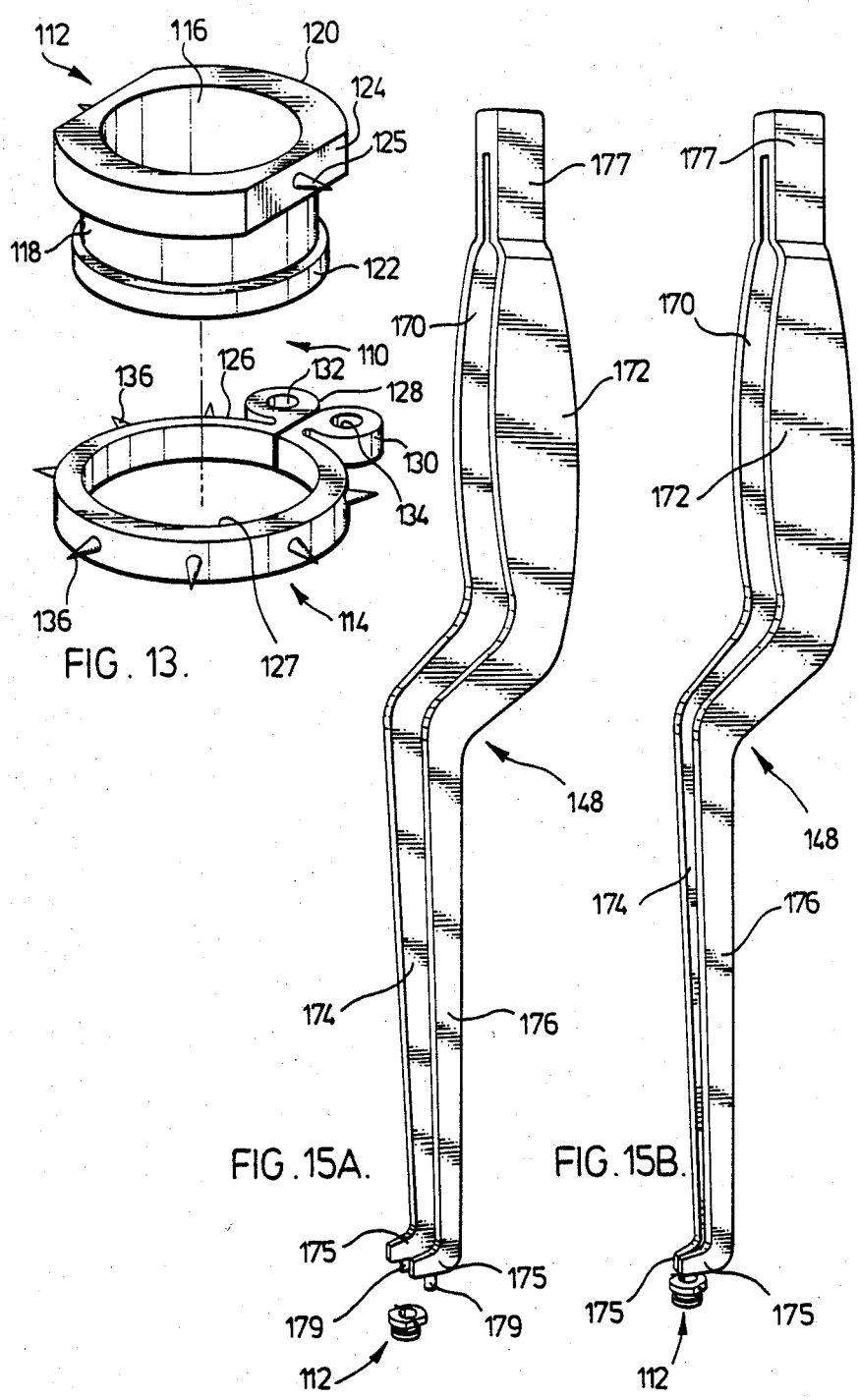

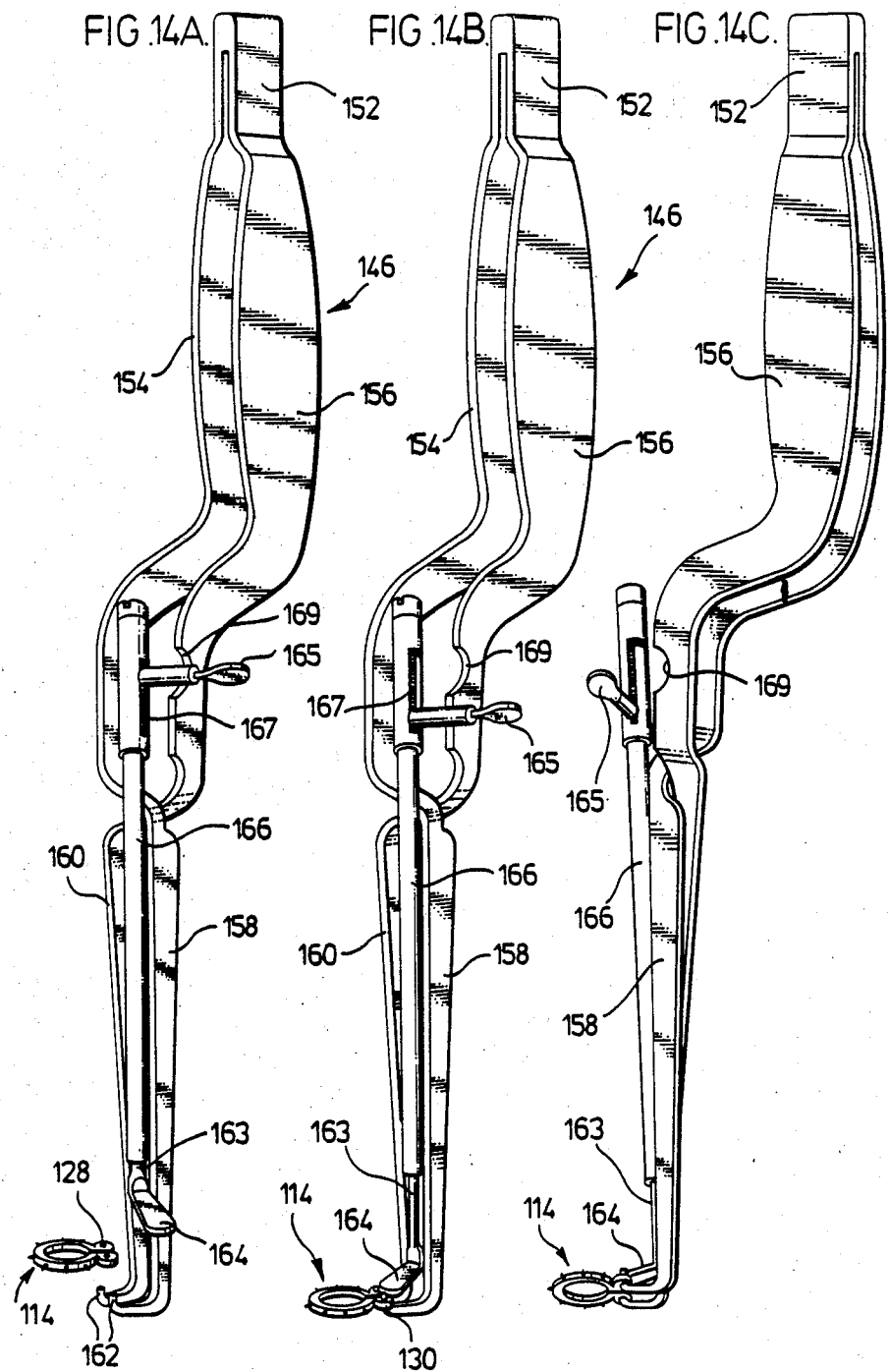

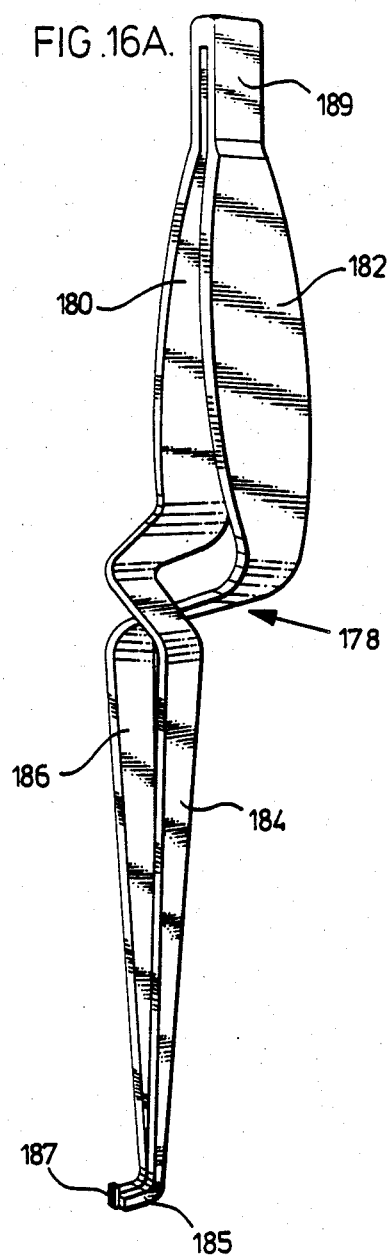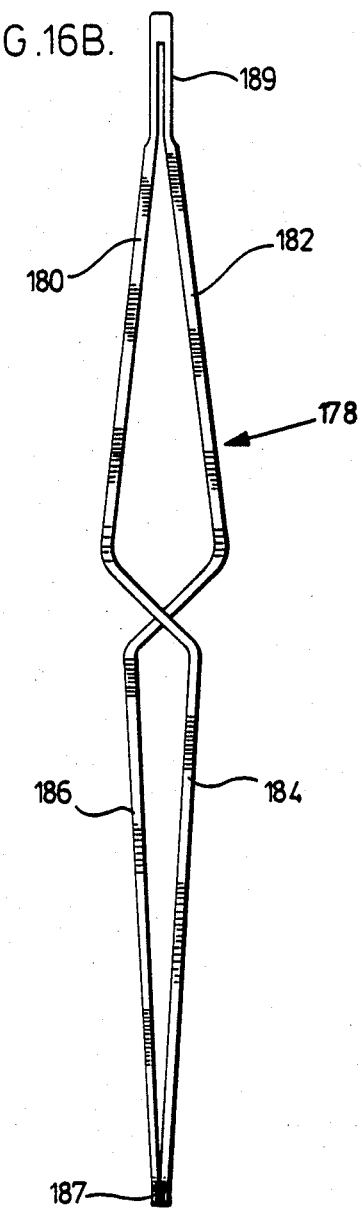

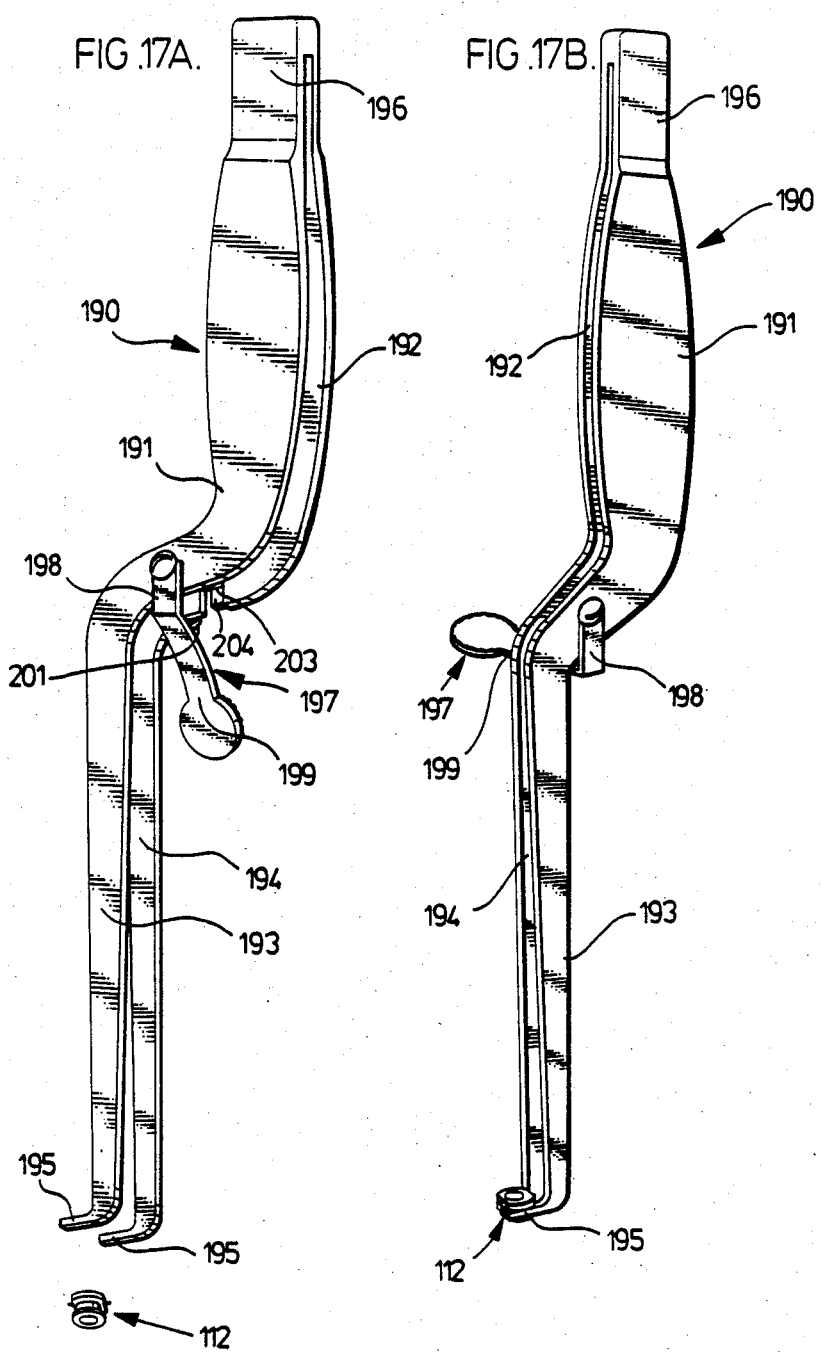

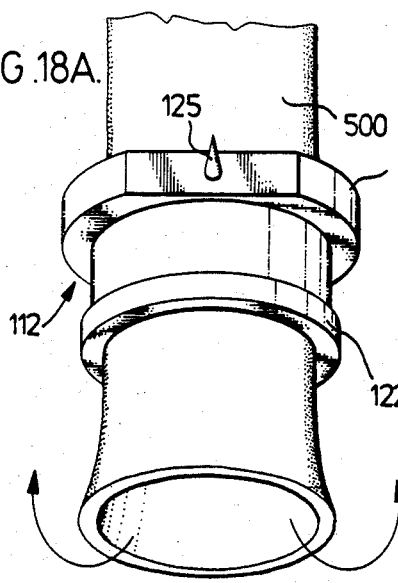
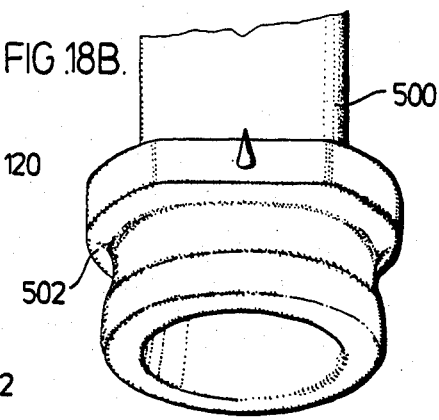
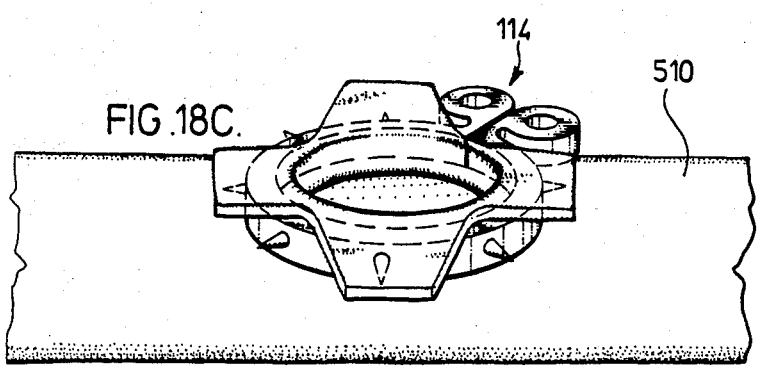
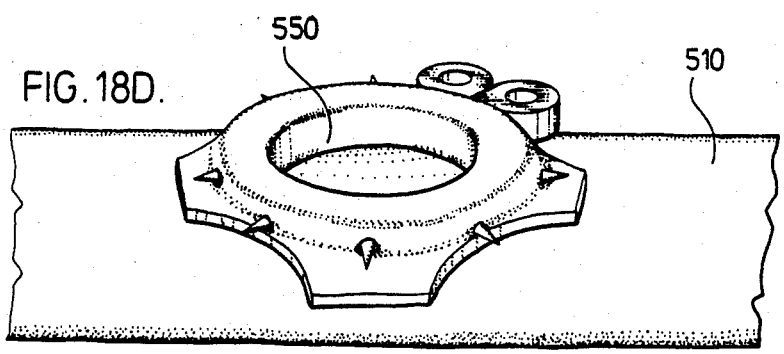

ANASTOMOSIS DEVICES AND KITS

BACKGROUND OF THE INVENTION (i) Field of the Invention

This invention relates to the connection of tubular tissue members, more especially blood vessels.

(ii) Description of the Prior Art

End-to-end connection of interrupted blood vessels in surgery is generally carried out by stitching with suture material.

Stitched connections are time consuming to complete, typically taking twenty minutes for each connection. While many surgeons have become adept in forming stitched connections, success is very much dependent on the skill of the individual surgeon.

The adaption of the operating microscope to the surgery of small vessels by Jacobson and Snarez in 1960 removed a barrier long believed insurmountable and showed that with intricate techniques and magnification successful suture anastomosis of vessels as small as 1 mm in diameter was possible.

Nevertheless, in spite of continuous training and the development of improved microscopes, instruments and sutures, many problems remain, and it remains difficult to obtain consistently high patency rates using suture techniques, particularly when dealing with vessels 1 to 2 mm in diameter.

The stitching of a connection between small diameter vessels in microsurgery presents special problems. The stitching operation is conducted under a microscope, often in a confined area.

Stitching also has the disadvantage that a foreign material, namely the suture is exposed at the interior blood contacting surface of the connection, and this presents a nidus for clot formation which in small vessel anastomosis is particularly likely to lend to occlusion. Proposals have been made for end-to-end stitchless connections, for example, in U.S. Pat. Nos. 3,155,095; 3,254,650; 3,254,651; 3,774,615 and 3,974,835. None of these prior proposals has proved to be practical and the prior devices have not been used in clinical applications.

In practice the handling and application of devices for stitchless connections is difficult. The devices are necessarily small in size since typically the vessels being connected have diameters in the range of 0.75 mm to 7.5 mm, and the vessel must not be unduly stretched.

It is extremely important that connections between blood vessels be complete and free of leaks. Failure of the connection results in internal bleeding which may be fatal.

There has been no previous proposal for an end-to-side non-suture anastomosis.

Stitchless connections provide the possibility of completing anastomosis in a much shorter time, more simply, while at the same time avoiding the presence of foreign material at the internal blood contacting surface of the connection.

SUMMARY OF THE INVENTION

It is an object of the invention to provide anastomosis devices for non-suture connection of tubular, tissue members, especially blood vessels.

It is yet another object of the invention to provide such devices for end-to-end and end-to-side connections.

It is a further object of this invention to provide an anastomosis kit comprising anastomosis devices for non-suture connections, and instruments for the handling and application of the devices.

It is yet another object of the invention to provide a non-suture, anastomosis method.

In accordance with one aspect of the invention there is provided an anastomosis device for non-suture end-to-end connection of tubular tissue members to be anastomosed comprising: a tubular connection member of sterilizable, biocompatible material having an inner cylindrical surface and an outer cylindrical surface; first and second, spaced apart clip-retaining means on said outer surface, first and second clip members, each clip member having a ring-shaped body part and opposed ends separable under spring tension, each body part defining a substantially circular opening, the body parts of said first and second clip members being adapted to circumferentially surround said outer cylindrical surface; said opposed ends having opposed handling elements to facilitate handling of said clip members and separation of said opposed ends for application of said clip members about said tubular connection; said clip-retaining means being effective to prevent axial dislodgement of the clip members, mounted on said connection member, at said first and second ends.

In accordance with another aspect of the invention there is provided an anastomosis device for non-suture end-to-side connection of tubular tissue members to be anastomosed comprising: a tubular connection member of sterilizable, biocompatible material having a smooth inner cylindrical surface, an outer cylindrical surface, and a clip retaining means on said outer cylindrical surface adjacent a first end of said connection member; clip means of sterilizable, biocompatible spring material having a ring-shaped body part defining a substantially circular opening, and opposed ends separable under spring pressure to enlarge said opening, said ring-shaped body part being adapted to circumferentially surround said outer cylindrical surface; a plurality of spaced apart tissue piercing and retaining members on said ring-shaped body part; said clip-retaining means being effective to prevent axial dislodgement of the clip member mounted on said tubular member, at said first end.

In accordance with yet another aspect of the invention there is provided an anastomosis kit for non-suture connection of tubular tissue members, which comprises a plurality of anastomosis devices of the invention of different sizes, a clip applicator comprising a pair of opposed legs connected at one end and having support means remote from said one end to supportingly engage the opposed handling elements of said clip members, said legs being operable under spring tension to separate said support means and the engaged opposed handling elements, to enlarge said substantially circular opening; and a holder for the connection members comprising a pair of opposed legs connected at one end and having opposed feet remote from from said one end, adapted to engage the inner cylindrical surface of a connection member of said devices, said holder legs being operable under spring tension to forcefully urge said feet in opposite directions against opposed sides of the inner cylindrical surface of said connection member.

In accordance with still another aspect of the invention there is provided a method of non-suture end-to-end anastomosis of tubular tissue members, which comprises: feeding a free end of a first tubular tissue member through a tubular connection member from a first end thereof; everting said free end over said connection member, from a second end thereof; holding the everted free end on said connection member, against anastomatic separation; applying a second tubular tissue member over the everted free end from said second end of said connection member; and holding said second member on said connection member, with said everted free end therebetween, against anastomatic separation.

In accordance with a further aspect of the invention there is provided a method of non-suture anastomosis of tubular tissue members which comprises: feeding a free end of a first tubular tissue member through a tubular connection member from a first end thereof; everting said free end over said connection member from a second end thereof, forming an expandible tissue opening in a side of a second tubular tissue member; expanding said tissue opening to receive said second end with the everted free end of said first tissue member; inserting said second end in said opening; and retracting said tissue opening into engagement with said everted free end.

In accordance with still another aspect of the invention there is provided an anastomosis device for non-suture end-to-end connection of tubular tissue members to be anastomosed comprising: a first support member having a first orifice therethrough for passage of an end of a first tubular tissue member, a second support member having a second orifice therethrough for passage of an end of a second tubular tissue member, said first support member having means to secure said end of said first tubular tissue member thereto, said second support member having means to secure said end of said second tubular tissue member thereto, and means adapted to hold said first and second support members in a first position in which the support means are in a substantially contacting relationship with said first and second orifices in alignment, and a second position in which said first and second support members are in spaced apart relationship.

In yet another aspect of the invention there is provided a method of non-suture end-to-end anastomosis of tubular tissue members, which comprises: disposing a free end of a first tubular tissue member through an orifice in a first support member, everting said free end over said first support member, disposing a free end of a second tubular tissue member through an orifice in a second support member, everting said free end over said second support member, and holding the everted ends of said tubular tissue members in contact against anastomatic separation.

BRIEF DESCRIPTION OF THE DRAWINGS

The invention is illustrated in particular and preferred embodiments by reference to the accompanying drawings in which:

FIGS. 4A, 4B, 4C and 4D are different views of a cylinder holder for use with the connection cylinder of FIG. 2;

FIGS. 5A, 5B, 5C and 5D are different views of a clip applicator for use with the clip of FIG. 3;

FIGS. 8 to 12 show sequential steps in an anastomosis procedure of the invention; in particular FIG. 8 illustrates the step of measuring the internal diameter of the separated ends of an artery which are to be connected by a vein;

FIG. 10 shows the vein having connection cylinders secured at both ends, ready to be anastomised at one end to the artery;

FIG. 11 shows the anastomization of one end of the artery to the vein; and

FIG. 12 shows the completed anastomosis between the vein and the separated ends of the artery;

FIG. 13 shows an anastomosis device for end-to-side anastomosis;

FIGS. 14A, 14B and 14C show a bayonet clip holder for use in applying a clip of the device of FIG. 13;

FIGS. 15A and 15B show a bayonet cylinder holder for use with the cylinder of FIG. 13;

FIGS. 16A and 16B show an alternative bayonet clip holder;

FIGS. 17A and 17B show a perimeter cylinder holder for use with the device of FIG. 13;

FIGS. 18A to 18E illustrate schematically the technique of end-to-side anastomosis in accordance with the invention;

FIG. 19 shows the formation of openings in arteries to be connected;

FIG. 20 shows the mounting of a clip in a first artery;

FIG. 21 shows the completion of the connection between the bridging vein and the second artery; and FIG. 22 shows the completed connection;

DESCRIPTION OF THE PREFERRED EMBODIMENTS WITH REFERENCE TO THE DRAWINGS

Figure 1:
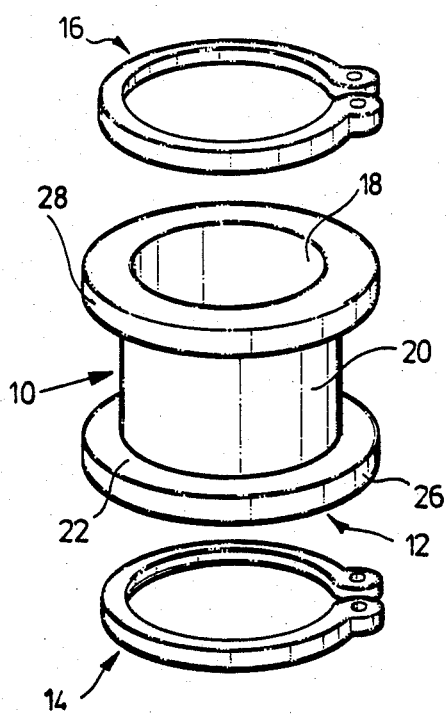
FIG. 1 illustrates an anastomosis device of the invention for end-to-end anastomosis.
Figure 2:
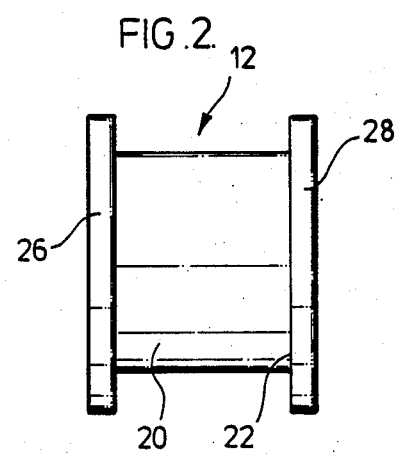
FIG. 2 shows a connection cylinder, a component of the device of FIG. 1.
Figure 3:
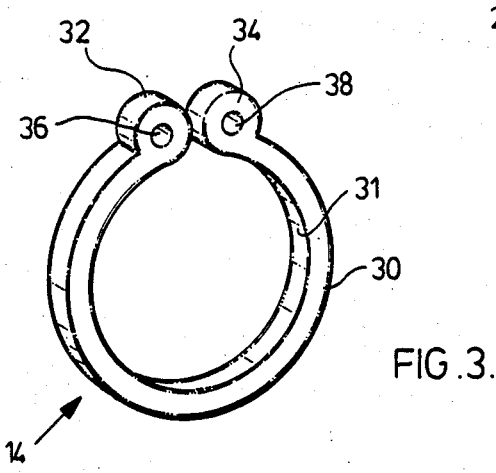
FIG. 3 shows a spring clip, a component of the device of FIG. 1.

With further reference to FIGS. 1, 2 and 3, a device 10 for end-to-end anastomosis comprises a tubular connection member in the form of a connection cylinder 12 and spring clips 14 and 16 which suitably are coded, for example, by colour coding, to identify either the cardiac or peripheral ends of a vein.

With further reference to FIGS. 1 and 2, the connection cylinder 12 comprises a smooth inner cylindrical surface 18 and a smooth outer cylindrical surface 20. An annular channel 22 in outer surface 20 extends between a first annular flange 26 and a second annular flange 28; the annular flanges 26 and 28 extend generally radially of the outer surface 20.

With further reference to FIG. 3, spring clip 14 comprises a ring-shaped body 30 defining a generally circular opening 31, and opposed clip ends 32 and 34. The clip ends 32 and 34 include eyelets 36 and 38, respectively.

Spring clip 16 is generally identical to spring clip 14 and suitably may be slight larger.

With reference to FIG. 4, FIG. 4A shows a cylinder holder 40 having legs 42 terminating in holder feet 44, each holder foot 44 having an outer cylindrical surface 46. Legs 42 are joined under spring tension at head 48.

FIGS. 4C and 4D show the cylinder holder 40 supporting the connection cylinder 12 of FIG. 2, with the cylindrical surfaces 46 of feet 44 engaging inner surface 18 of connection cylinder 12 under spring tension.

FIGS. 5A to 5D show a clip applicator 50. With particular reference to FIGS. 5A and 5B, applicator 50 comprises legs 52 and 54 terminating in crossed arms 56 and 58, respectively. Legs 52 and 54 are connected, under spring tension at applicator head 64, and spikes 60 and 62 extend from arms 56 and 58, respectively.

FIGS. 5C and 5D show clip applicator 50 supporting a clip 14 of FIG. 2, with the spikes 60 and 62 extending through eyelets 36 and 38, respectively.

Figure 6A:
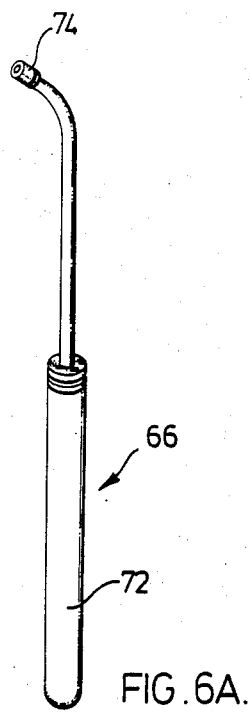
FIGS. 6A and 6B illustrate an obturator for use in the invention.
Figure 6B:
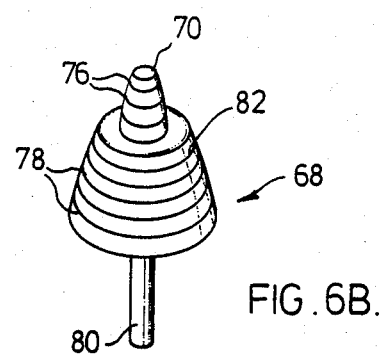

With reference to FIG. 6A handle element 66 comprises an elongated handle 72 and a tubular end 74. FIG. 6B shows an obturator 68 having a generally conical end portion 70 comprising annular segments 76 of different defined diameters, and a truncated cone portion 82 comprising annular segments 78 of different defined diameters. A spigot 80 extends from obturator 68.

Suitably the annular segments 76 and 78 have diameters ranging from 0.5 to 4.5 mm, the diameters of adjacent segments 76 and 78 increasing in increments of 0.5 mm with increase in distance from the spigot 80.

Figure 7A:
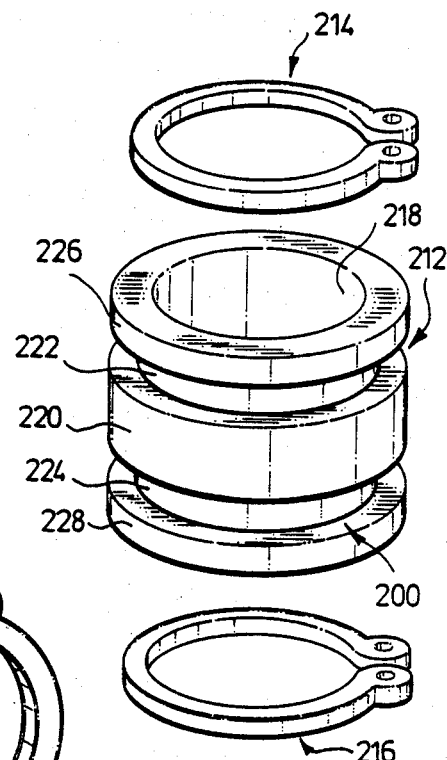
FIGS. 7A and 7B illustrate an anastomosis device of the invention for end-to-end anastomosis, in a different embodiment.
Figure 7B:
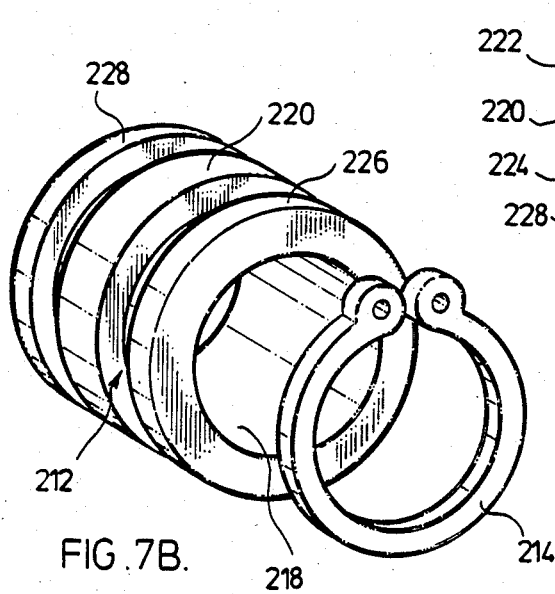

With reference to FIGS. 7A and 7B a device 200 for end-to-end anastomosis comprises a tubular connection member in the form of a connection cylinder 212 and spring clips 214 and 216 which are essentially the same as clips 14 and 16 described with reference to FIGS. 1 to 3.

The connection cylinder 212 has a smooth inner cylindrical surface 218 and a smooth outer cylindrical surface 220. Generally parallel annular grooves 222 and 224 are formed in outer surface 220 and define first and second ends 226 and 228 in surface 220.

The anastomosis method for end-to-end connection is further described with reference to FIGS. 8 to 12 which illustrate a method for forming an anastomosis between ends 84 and 86 of an artery 85; the anastomosis being carried out with a vein 92 which is to form a bridge between ends 84 and 86.

The anastomosis method is described by reference to the device 100 of FIGS. 1 to 3 but the device 200 of FIGS. 7A and 7B could be employed in a similar manner.

In a first step an appropriate vein 92 for the anastomosis is selected, is tagged to identify the cardiac end and is then removed from the body.

The internal diameter of the vein 92 and its radial stretchability is measured using an obturator of the type illustrated in FIGS. 6A and 6B.

The artery 85 to be used is exposed and the free separated ends 84 and 86 are supported between clamps 88 and bridge support 90.

In order to select a connection cylinder 12 of appropriate size a comparison is made between the stretch diameter of the vein 92 and the internal diameter of the artery 85.

Figure 8:
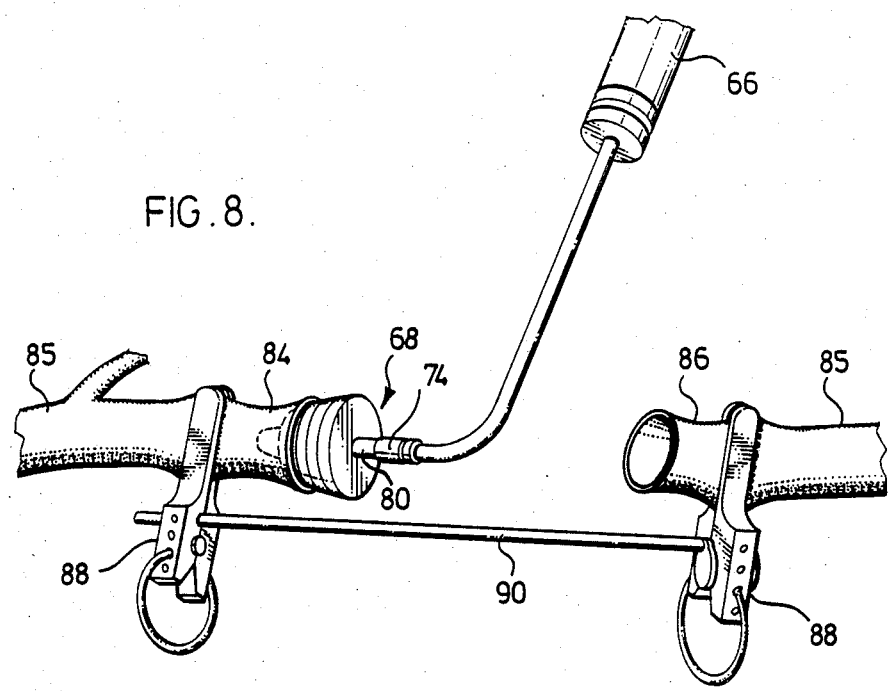

FIG. 8 particularly illustrates the use of an obturator 68 of FIG. 6B to measure the internal diameter of artery 85 at end 84. Obturator 68 is secured to handle element 66 by inserting spigot 80 in tubular end 74. The obturator 68 is inserted into the open end 84 of artery 85. The annular segments 76 and 78 are of different specified diameters. In this way an unstretched and stretched diameter of the artery 85 can be determined. The unstretched and stretched diameters of the vein 92 are determined in a similar manner (not illustrated).

A connection cylinder 12 having an appropriate diameter is then selected.

Figure 9A:
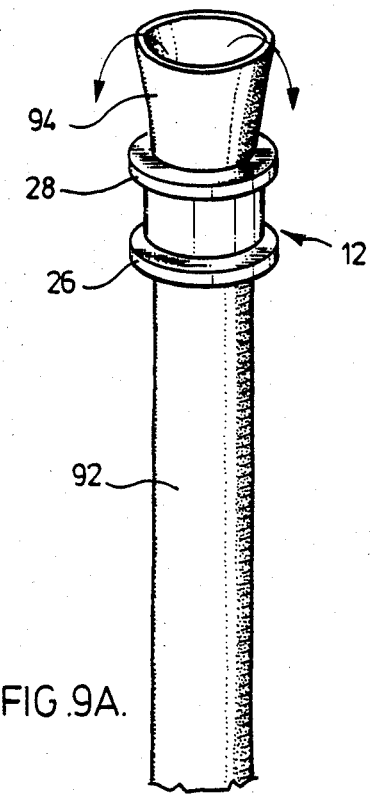
FIGS. 9A and 9B show application of parts of the device of FIG. 1 to the vein.
Figure 9B:
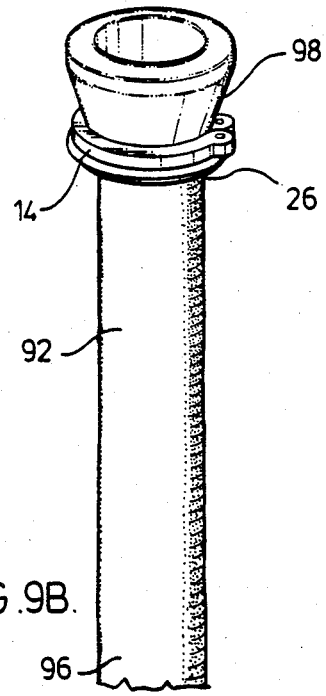

FIGS. 9A and 9B show schematically the application of connection cylinder 12 to one end of vein 92. As shown in FIG. 9A vein end 94 of vein 92 is passed through a first end adjacent flange 26 and emerges from a second end adjacent flange 28 of connection cylinder 12. Vein end 94 is then everted over connection cylinder 12 in the manner indicated by the arrow in FIG. 9A. The everted portion 98 extends over annular channel 22 in the direction of flange 26. A spring clip 14 is then seated in annular channel 22 adjacent flange 26 with the everted portion 98 of vein 92 thereunder.

It will be understood that the circular opening 31 of spring clip 14 has a diameter selected having regard to the size of connection cylinder 12. The spring tension in spring clip 14 in conjunction with the diameter of circular opening 31 and the depth of annular groove 32 are such that ring-shaped body part 30 is firmly seated in annular channel 22 and the everted portion 98 is securely held on connection cylinder 12 against anastomatic separation. In other words, the everted portion 98 is firmly held on cylinder 12 under spring pressure, and will not become separated from the cylinder such as to permit leakage of blood at the connection.

Figure 10:
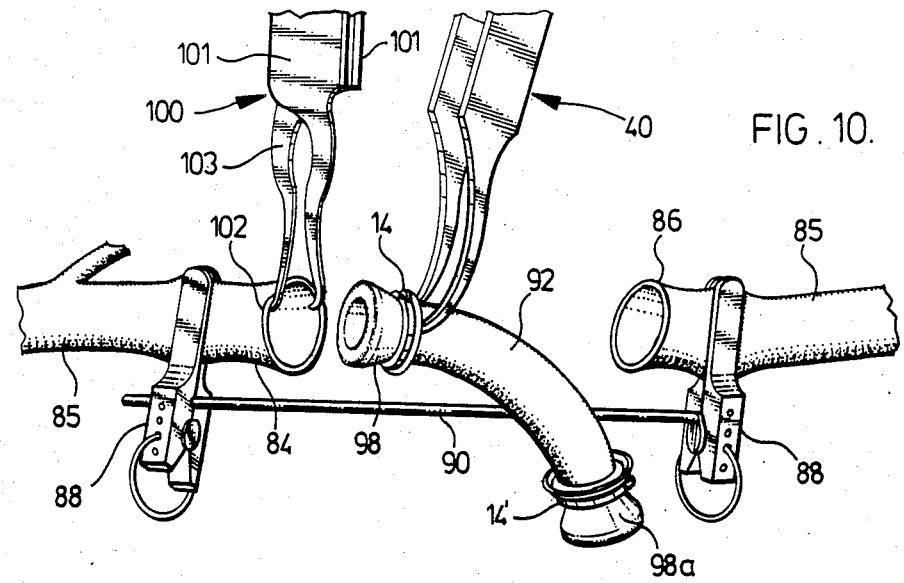

Vein end 96 is mounted on a second connection cylinder 12 in the same manner, but employing a spring clip 14' over everted portion 98a (see FIG. 10). Spring clips 14 and 14' are coded differently for use with different ends of the vein 92, so that rapid identification of the cardiac and distal ends of the vein may be achieved, for correct orientation of vein 92.

With further reference to FIG. 10, the vein 92 has cylinders 12 (not visible) mounted at its ends 94 and 96 (see FIGS. 9A and 9B), and secured by coded spring clips 14 and 14', respectively. One cylinder 12 is held by a curved cylinder holder 40 (see FIGS. 4A to 4D) which engages the interior thereof, and the end 84 of artery 85 is held open by forceps 100 having hook ends 102 which pierce the walls of artery end 84. The cylinder 12 with everted portion 98 is inserted into the artery 85 at end 84.

Figure 11:
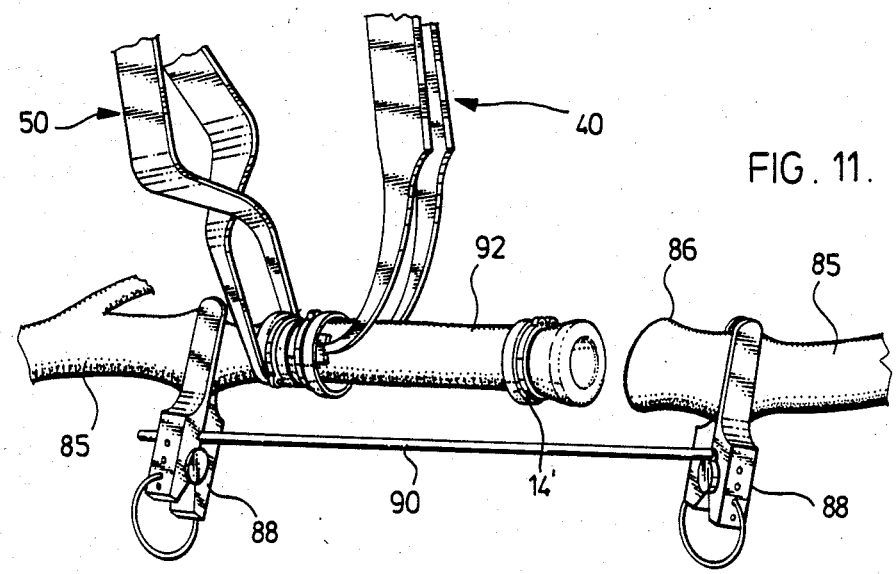

With reference to FIG. 11, insertion into end 84 is completed.

Referring particularly to FIGS. 5A, 5B, 5C and 5D, spikes 60 and 62 of applicator 50 are inserted through eyelets 36 and 38 of spring clip 16. When legs 52 and 54 of applicator 50 are urged together arms 56 and 58 separate thereby separating clip ends 32 and 34, under spring tension, with enlargement of circular opening 31.

With clip ends 32 and 34 separated, and opening 31 enlarged, the clip 16 is applied over artery end 84 and is seated over everted portion 98 in the annular groove 22 adjacent flange 28. Release of the inward pressure on legs 52 and 54 urges clip ends 32 and 34 towards each other under the spring tension of ring-shaped body 30. The size of circular opening 31, the spring tension of clip 16 and the depth of annular channel 22 in conjunction with the thickness of everted portion 98 are selected such that spring clip 16 is firmly seated in annular channel 22 and holds artery end 84 on connection cylinder 12 with everted portion 98 therebetween against anastomatic separation.

The flanges 26 and 28 prevent axial dislodgement of the clips 14 and 16 from cylinder 12, and the pressure of the clips 14 and 16 on the underlying vein and artery walls holds the vein and artery walls in contact on the connection cylinder 12 against anastomatic separation.

Figure 12:
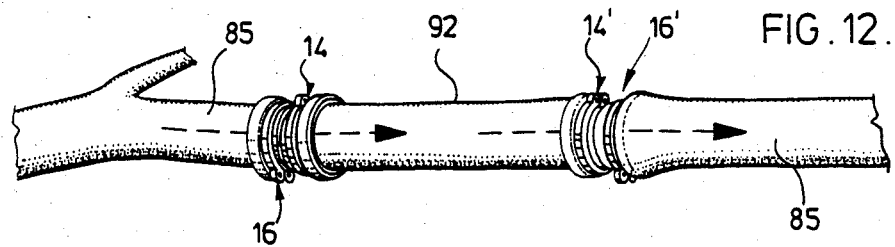

The procedure is repeated to secure the vein 92 within artery end 86 employing spring clip 16' to complete the anastomosis as illustrated in FIG. 12.

The curved cylinder holder 40 (FIGS. 4A to 4D) comprises legs 42 and feet 44 adapted to engage the inner surface of cylinder 12, with vein 92 thereon. Legs 42 are connected under spring tension. In use the feet 44 are located on opposed inner sides of cylinder 12 and are brought into contact therewith by spring tension on the inner cylinder walls urging legs 42 away from each other.

Forceps 100 have legs 101 and crossing arms 103. Legs 101 are connected under spring tension; finger pressure on legs 101 urging them together produces separation of arms 103 with hook ends 102 so that artery end 84 is opened.

In the case of the device 200 of FIGS. 7A and 7B the clips 214 and 216 are firmly seated in annular grooves 222 and 224 and hold the tissue material of the artery and vein in connection member 212 and in contact with each other against anastomatic separation. The depth and width of grooves 222 and 224 may be selected such that clips 214 and 216 may be securely seated in grooves 222 and 224 with the underlying tissue material, whereby axial dislodgement of the clips 214 and 216, and anastomatic separation is avoided.

The device 10 of FIGS. 1 to 3 is appropriate for the anastomosis of tubular vessels having a diameter above about 2.5 mm; the device 200 of FIGS. 7A and 7B is especially appropriate for microanastomosis, i.e. anastomosis of vessels having a diameter of 1 to 2 mm. The thickness of the tubular vessel wall increases with vessel diameter, and greater care is needed with vessels having thinner walls in ensuring that the vessel wall is not damaged as a result of stretching, during the eversion of the vessel end over the connection cylinder.

In the case of device 200 the diameters of the inner and outer cylindrical surfaces 218 and 220 are selected having regard to the diameter of the vessel to be everted thereon, the diameter of surface 220 being only slightly greater than that of surface 218, and the diameter of the ends 226 and 228 is the same as that of the outer cylindrical surface 220. Thus in microanastomosis no damage is caused to the relatively thin vessel walls as a result of stretching of the vessel ends over the ends 226 and 228. The relatively shallow grooves 222 and 224 in conjunction with the clips 214 and 216 are adequate to prevent axial or radial movement of the anastomosed vessels.

In the case of device 100 of FIGS. 1 to 3, the thicker vessel walls of the larger size vessels are less susceptible to damage when being stretched over cylinder 12. The annular channel 22 is relatively deep or otherwise stated the diameter of flanges 26 and 28 is significantly larger than the diameter of outer surface 20; the diameter of outer surface 20 being only slightly larger than the diameter of inner surface 18.

Thus the depth of channel 22 forming relatively large diameter flanges 26 and 28 compensates for the absence of discrete annular grooves similar to grooves 222 and 224 in the device 200, to accommodate clips 14 and 16. The flanges 26 and 28 defined by the deep channel 22 serve to prevent axial dislodgement of clips 14 and 16 from cylinder 12; and in addition their relative diameter is such that even if some radial opening or displacement of the clips 14 and 16 occurs, the partially opened clips 14 and 16 will not pass over flanges 26 and 28.

The relatively deep channel 22 also serves to accommodate any bunching or folds of thicker walled vessels, and ensures that such folds are held on the cylinder 12 between flanges 26 and 28.

The device 200 can also be employed for anastomosis of larger vessels, however, the device 10 is found to be less suitable for microanastomosis.

With further reference to FIG. 13, a device 110 for end-to-side anastomosis comprises a tubular connection member in the form of a connection cylinder 112 and spring clip 114.

Connection cylinder 112 has a smooth inner cylindrical surface 116, a smooth outer cylindrical surface 118 and annular flanges 120 and 122 at opposed ends. Annular flange 120 has opposed flat walls 124 and a spike 125 extending from each wall 124.

Spring clip 114 includes a ring-shaped body 126 defining a substantially circular opening 127, and clip ends 128 and 130 having eyelets 132 and 134, respectively.

Tines 136 extend substantially radially outwardly from ring-shaped body 126.

The cylinder 112 is suitably made of stainless steel. The flange 120 prevents the donor vessel and cylinder 112 from slipping into the lumen of the recipient vessel. Outer cylindrical surface 118 is suitably of relatively short length so that clip 114 may fit snugly between flanges 120 and 122 and prevent protrusion of the graft donor vessel into the lumen of the recipient vessel.

With further reference to FIGS. 14A to 14C a bayonet clip applicator 146 comprises legs 154 and 156 joined under spring tension at head 152. Crossing arms 158 and 160 extend from legs 154 and 156, respectively and terminate in spikes 162.

A spring loaded stabilizer arm 163 having a spring 167 extends between legs 154 and 156, and arms 158 and 160, in a casing 166, and terminates in a stabilizer foot 164.

Stabilizer arm 163 includes a locking arm 165 which engages a recess 169 in leg 156 to firmly locate arm 166.

Stabilizer arm 163 is urged downwardly by spring 167 but is restrained against downward movement, as shown in FIG. 14A, by locking arm 165 which engages recess 169. When locking arm 165 is released from recess 169 the stabilizer arm 166 moves downwardly under the action of spring 167 and stabilizer foot 164 lightly engages clip ends 128 and 130 of clip 114 and stabilizes the location of clip 114 during the enlargement of opening 127 and insertion of the cylinder 112. The opening 127 is enlarged for the insertion of cylinder 112 by pressing legs 154 and 156 towards each other.

With further reference to FIGS. 15A and 15B, a bayonet cylinder holder 148 comprises upper legs 170 and 172 and lower legs 174 and 176 terminating in holder feet 175. Legs 174 and 176 are off-set relative to legs 170 and 172.

The holder feet 175 have toes 179 with outer cylindrical surfaces for engaging the inner surface 116 of cylinder 112.

Upper legs 170 and 172 are connected at head 177 under spring pressure.

The off-setting of legs 174 and 176 relative to head 177 and legs 170 and 172 avoids obstruction in the line of vision of the surgeon.

With further reference to FIGS. 16A and 16B there is shown an alternative bayonet clip applicator 178. Applicator 178 has legs 180 and 182 and crossing arms 184 and 186 terminating in feet 185 having spikes 187. Legs 180 and 182 are connected under spring tension at head 189.

Applicator 178 functions in the same manner as applicator 50 in FIGS. 5A, 5B, 5C and 5D, however, the off-setting of arms 184 and 186 relative to legs 180 and 182 avoids obstruction in the line of vision of the surgeon.

With further reference to FIGS. 17A and 17B a perimeter cylinder holder 190 comprises upper legs 191 and 192 and lower legs 193 and 194 terminating in feet 195. Legs 193 and 194 are off-set relative to legs 191 and 192.

Legs 191 and 192 are connected at head 196 under spring pressure.

A spring leaf locking arm 197 includes an upper arm 198 mounted on leg 191 and a lower arm 199 having a projecting stop 201. A recess 203 having a stop 204 is defined in leg 192.

Feet 195 are urged apart by the spring pressure as shown in FIG. 17A. Legs 191 and 192 are urged towards each other by finger pressure until feet 195 engage opposed outer sides of cylinder 112, and are locked in position under the spring action of arm 197 urging lower arm 199 into recess 203, where it is held by engagement of stops 201 and 204.

With reference to FIGS. 18A, 18B, 18C, 18D and 18E, the end-to-side anastomosis technique is illustrated schematically.

FIGS. 18A and 18B show the mounting of a vein 500 on connection cylinder 112 of FIG. 13, the everted portion 502 being held by the spikes 125.

FIGS. 18C and 18D show the mounting of a clip 114 around an opening in an artery 510 to form a circular opening corresponding to opening 127 of clip 114, and bounded by tissue annulus 550.

Figure 18E:
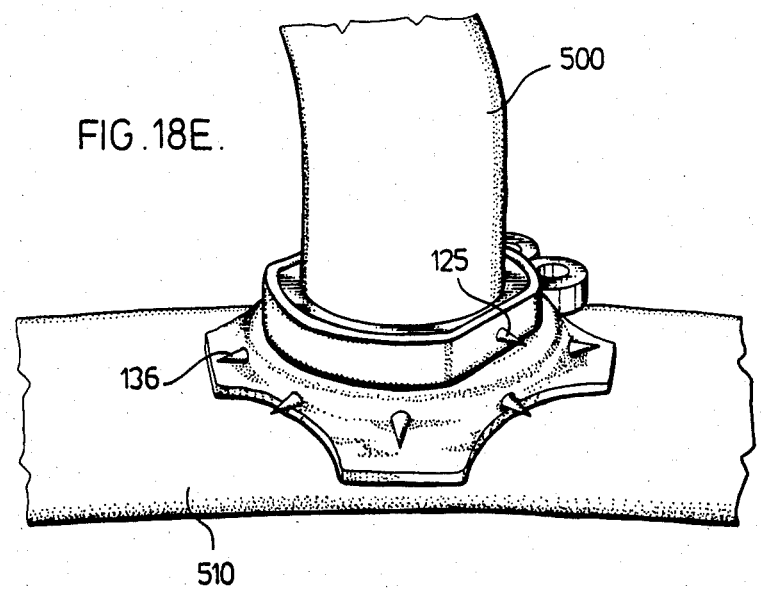

FIG. 18E shows the completed anastomosis in which flange 122 of cylinder 112 is disposed below clip 114 and prevents axial dislodgement of clip 114.

The end-to-side anastomosis technique is illustrated in a stepwise fashion in FIGS. 19 to 22.

Flow of blood is interrupted in arteries 510 to 512 to be connected, by means of clamps 544; a vein 500 is to be anastomosed between the arteries 510 and 512.

Figure 19:
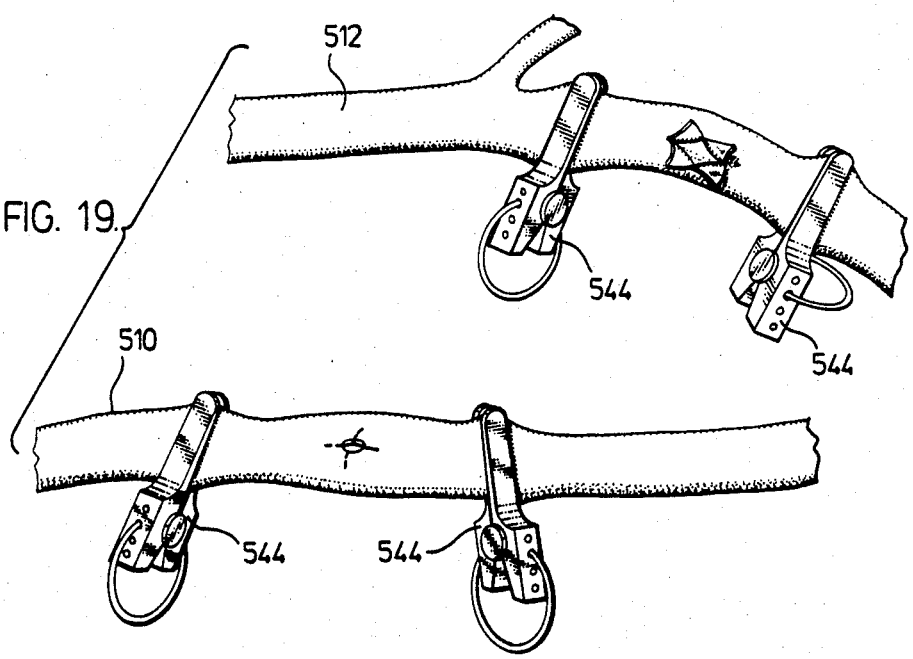
FIGS. 19 to 22 show sequential steps in an anastomosis procedure of the invention, in particular.

As shown in FIG. 19 an opening is formed in each of arteries 510 and 512 suitably by applying two incisions at right angles forming a cross in the tissue material (see artery 510 in FIG. 19). The artery tissue adjacent the incisions is folded back (see artery 512 in FIG. 19).

Figure 20:
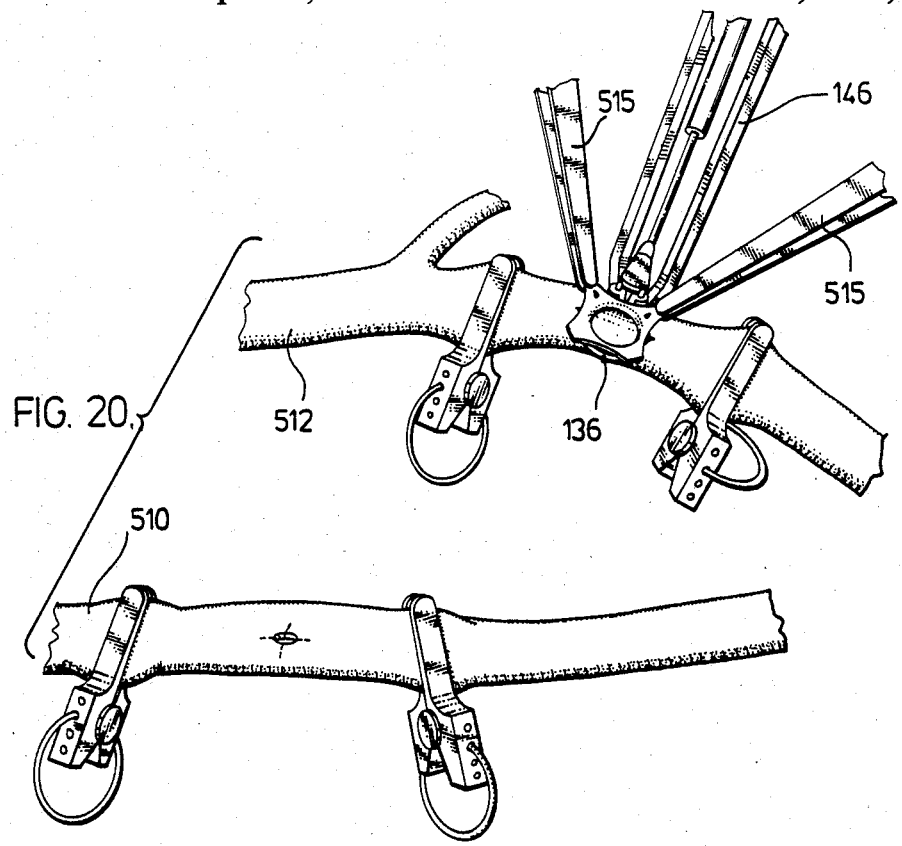

With reference to FIG. 20, the folded back tissue of artery 512 is inserted upwardly through opening 127 in clip 114 and is secured over ring shaped body 126 by the tines 136 as illustrated schematically in FIGS. 18C and 18D. Forceps 515 are employed to draw the folded back tissue over the tines 136. During this operation the clip 114 is supported by the clip applicator 146 of FIGS. 14A to 14C.

There is thus formed a generally, circular expandible tissue opening into artery 512 corresponding to circular opening 127 of clip 114, and bounded by tissue annulus 550.

An end of vein 500 is passed through connection cylinder 112 and everted thereover in the general manner illustrated in FIGS. 18A and 18B, the vein 500 being everted over the flanges 120 and 122 and being pierced by spikes 125 to form the everted portion 502.

Figure 21:
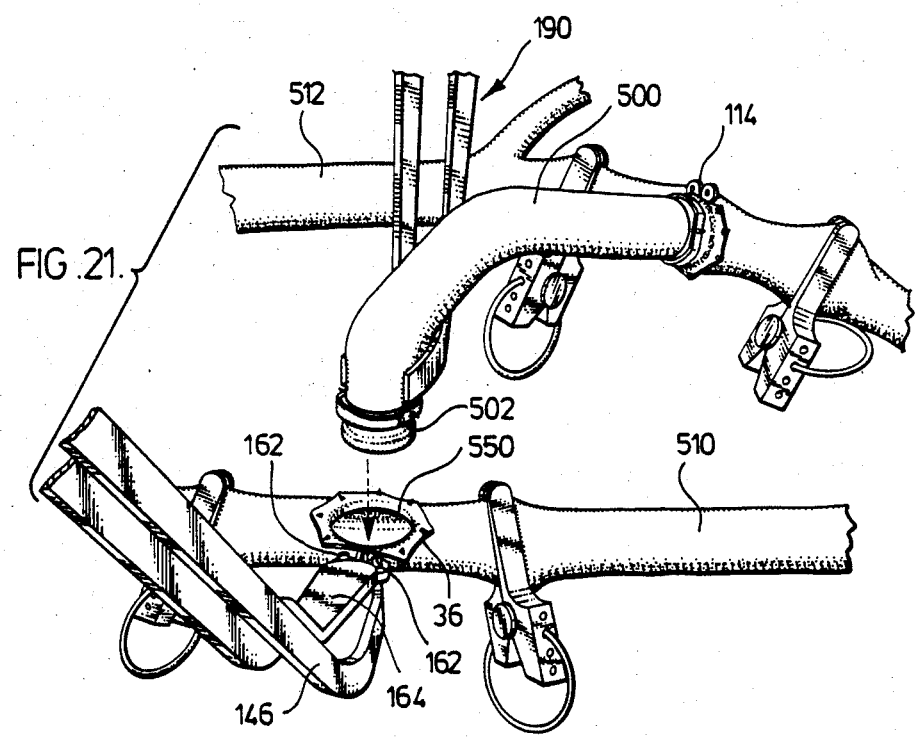

A final stage of the anastomosis is illustrated in FIG. 21, wherein the connection of vein 500 to artery 512 is already completed and a similar connection between vein 500 and artery 510 is about to be completed.

As shown in FIG. 21 eyelets 132 and 134 of clip 114 mounted in artery 510 are engaged by the spikes 162 of bayonet clip applicator 146.

Inward pressure on legs 154 and 156 of applicator 146 causes spikes 162 to separate, thereby separating clip ends 128 and 130 and enlarging circular opening 127 which in turn enlarges the diameter of tissue annulus 550.

Cylinder 112 with vein 500 mounted thereon is held by bayonet perimeter cylinder holder 190 (see FIGS. 17A and 17B) and is then inserted into the enlarged opening 127 so that flange 122 of cylinder 112 is disposed on the interior side of ring-shaped body 126 (see FIG. 18E), within artery 510 and ring-shaped body 126 is disposed about outer surface 118. During this insertion stabilizer arm 166 applies pressure on clip ends 128 and 130 to firmly position spring clip 114 for insertion of cylinder 112 and its mounted vein 500.

Thereafter pressure on legs 154 and 156 is released so that they move apart under spring pressure and arms 158 and 160 move towards each other to their normal position and clip ends 128 and 130 likewise are urged towards each other. In this way clip 114 is firmly located under spring tension over outer surface 118 with the everted portion 502 of vein 500 therebetween.

The flanges 122 and 120 and spikes 125 prevent axial separation of clip 114 from cylinder 112 and the pressure of clip 114 holds tissue annulus 550 in contact with the everted portion 502 of vein 500 whereby anastomatic separation is avoided.

The spring tension in body 126 and the dimensions of flange 122 are such that opening 127 can be enlarged to a diameter greater than that of flange 122 for insertion of cylinder 112 with vein 500 mounted thereon into tissue annulus 550.

Figure 22:
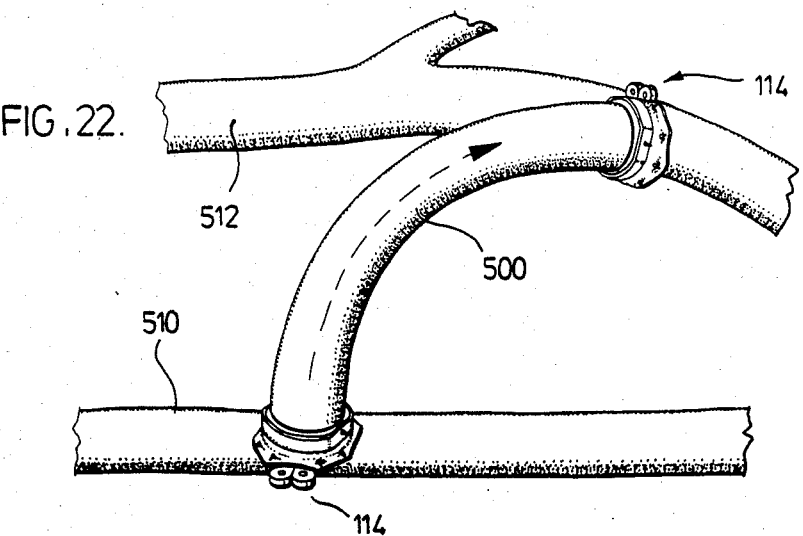

With further reference to FIG. 22, there is illustrated the completed end-to-side anastomosis.

Figure 23A:
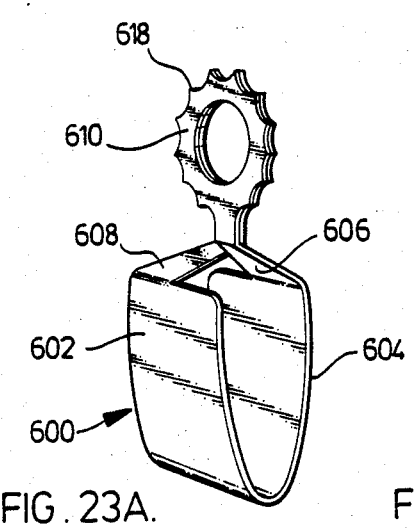
FIGS. 23A and 23B show another device for end-to-end anastomosis.
Figure 23B:
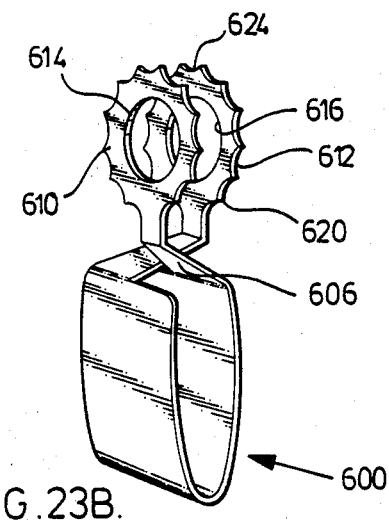

With further reference to FIGS. 23A and 23B there is shown an anastomosis clip 600 having a pair of legs 602 and 604 and cross-over arms 606 and 608. Arms 606 and 608 terminate in aligned rings 610 and 612. Rings 610 and 612 have circular orifices or openings 614 and 616 which form a continuous orifice 615.

Ring 610 has a plurality of spaced apart, outwardly extending teeth 618 and ring 612 has a similar plurality of teeth 620.

Legs 602 and 604 are connected at head 622 under spring pressure which tends to urge legs 602 and 604 away from each other, thereby urging rings 610 and 612 into contact with each other as shown in FIG. 23A. Pressure on legs 602 and 604 forces them together thereby forcing rings 610 and 612 apart, as shown in FIG. 23B.

A small gap 624 is defined in ring 612.

The anastomosis clip 600 is particularly suitable for anastomosis of vessels having a diameter greater than 2 mm.

Figure 24:
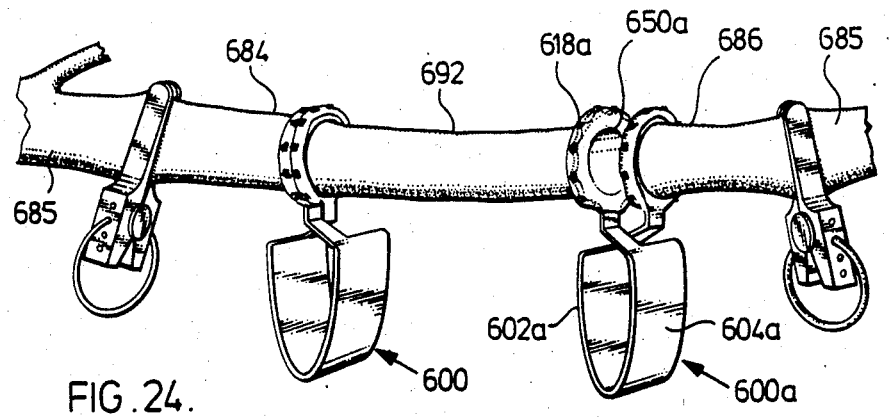
FIG. 24 shows the final stage of an end-to-end anastomosis employing the device of FIGS. 23A and 23B.

The anastomosis technique employing clips 600 is illustrated in FIG. 24 in which the separated ends 684 and 686 of an artery 685 are connected with a vein 692. In FIG. 24 the two clips are identical but for convenience the parts of one clip are additionally designated by the letter 'a'.

Clips 600 and 600a having orifices 615 and 615a are selected according to the dimensions of artery 685 and a vein 692 of appropriate dimensions is selected.

As shown in FIG. 24 the anastomosis of end 684 and vein 692 with clip 600 is complete; the technique is described by reference to the anatomosis of end 686 and vein 692 with clip 600a.

In the first stage of the anastomosis (not illustrated) the clips 600 and 600a are connected to the ends of vein 692, the artery end 684 is connected to clip 600 and finally the artery end 686 is connected to clip 600a.

In order to connect a free end of vein 692 to clip 600a, the surgeon squeezes legs 602a and 604a together to separate rings 610a and 612a.

The free end of vein 692 is fed through orifice 614a of ring 610a and is everted over teeth 618a thereby forming an annulus of vein tissue 650a.

In the final stages (illustrated in FIG. 24) the end 686 of artery 685 is feed into orifice 616a, and is everted over teeth 620a thereby forming an annulus of artery tissue 652a.

The pressure urging legs 602a and 604a together is released so that rings 610a and 612a are urged towards each other whereby annulus 650a firmly contacts annulus 652a, the annuli 650a and 652a being held against anastomatic separation by the spring pressure.

Similar annuli 650 and 652 are held together by clip 600, and in this way a continuous wall of tissue material is formed between artery ends 684 and 686 and normal flow of blood can resume.

It will be recognized that in both the end-to-end anastomosis illustrated in FIGS. 8 to 12; and the end-to-side anastomosis illustrated in FIGS. 19 to 22, there is no exposure of devices 10 and 110 at the lumen, or interior wall of the arteries and veins. This represents a significant advantage over conventional suture techniques.

The anastomosis technique has been particularly described, with reference to the drawings, for the joining of completely separated vessel ends. It is, however, possible to employ the same devices and techniques to complete a connection between a partly separated wall of a tubular vessel. For example, when an aneurysm occurs, the artery wall bulges and creates a weak spot in the wall which may burst under the pressure of the blood. In accordance with the invention the artery may be partially severed around the aneurysm and the separated edges of the artery wall may be joined using the devices of the invention to by-pass the aneurysm.

In this case the gap 624 in ring 612 of clip 600 may serve for introduction of the unsevered portion of the artery into clip 600.

Employing the anastomosis devices and instruments of the invention the surgeon can readily hold and support the devices during the anastomosis. It will be understood that the surgeon is working in a very small area under a microscope, and so in developing a satisfactory and practical technique it is important that one person, namely the surgeon, be able to hold and apply the principal components of the anastomosis devices during the anastomosis.

For example, in end-to-end anastomosis, it is necessary that the connection cylinder be held still during application of the spring clip. By means of the instruments of the invention the surgeon is able to hold the connection cylinder with the everted vein with one hand for insertion of the cylinder into the artery held open with the other hand. Still holding the cylinder inserted in the artery with one hand, the surgeon can hold the spring clip and open and apply it with the other hand. In this regard it has been found to be particularly important that the person holding the cylinder also applies the spring clips so that his hands remain axial and the cylinder is mounted on the true axis of the artery to be anastomosed.

One of the shortcomings of prior proposals for non-suture anastomosis has been the absence of instruments to hold, support and apply the devices. This is especially important since the anastomosis devices are of very small size being intended for connecting vessels having diameters of 0.75 to 7.5 mm. The kit of the invention thus represents an especially important embodiment of the invention.

The anastomosis procedure of the invention has also been made applicable to microanastomosis and to long vein intercranial bypass procedures. For this purpose cylinder holders and clip applicators have been developed suitable for use in fine deeply situated regions at the base of the brain. To meet these purposes instruments have been developed of increased length and incorporating a bayonet design to allow a more direct, unobstructed, view and facilitate anastomosis.

The bayonet cylinder holder described above has its cylinder engaging end offset relative to the handle, thus the handle does not obstruct the surgeon's view of the anastomosis site. The bayonet cylinder holder is thus especially suitable in microanastomosis of 1 mm vessels in a confined space.

By way of example, connection cylinders 12 and 112 typically have diameters of 3.5 mm, 3 mm, 2.5 mm, 2 mm, 1.5 mm, 1.0 mm and 0.75 mm, with a wall thickness of 5 thousandths of an inch. The length of the connection cylinder is suitably of the same order as the diameter. Suitably the cylinders are made of stainless steel.

Spring clips 14 and 16 are suitably of metal or metal alloy wire, for example, Elgiloy wire, typically having a wire diameter of 7 to 18 thousandths of an inch. Typically these clips may have diameters of 3.5 mm, 3 mm, 2.5 mm, 2 mm, 1.5 mm, 1.0 mm and 0.75 mm.

Elgiloy is a cobalt base alloy of the following composition in weight %:

| | |
|---|---|
| Co | 40% |
| Cr | 20% |
| Ni | 15% |
| Mo | 7% |
| Mn | 2% |
| Be | 0.4% |
| C | 0.15% |
| Fe | 15.81% |

The clips fabricated from the wire as suitably heat-treated to provide spring tension characteristics. By way of example the clips are heated with a propane torch to a light straw colour at an elevated temperature.

Employing the non-suture technique of the invention the surgeon can complete a connection much more rapidly than with conventional techniques and has the significant advantage of intima to intima contact at the site of anastomosis with no foreign material exposed to the lumen of the vessels being joined. In particular employing the non-suture technique of the invention the surgeon can complete a connection regardless of vessel size, including a microvascular anastomosis of 1 mm diameter vessels typically in a time of less than three minutes. Such microvascular anastomosis employing conventional suture techniques, even with use of a microscope, requires a significantly longer time, typically 20 to 40 minutes.

RESULTS

End-to-End

Table I shows the results of in vivo end-to-end anastomosis in dogs employing the procedure and devices of the invention. Seventeen vascular anastomoses are carried out in five dogs. Carotid, femoral and axillary vessels were used with diameters ranging from 2 to 3.5 millimeters. Control angiograms were taken, following anastomosis, for selected animals. The patency rate in the anastomoses that have had post-operative angiography has been 91%. There has been only one anastomosis that has not been visualized on post-operative angiography and it is uncertain whether this is related to occlusion of the anastomosis or to technical factors in performing the angiogram.

TABLE 1

| DOG NO. | VESSEL | DIAMETER (mm) | PATENCY (angio) |
|---|---|---|---|
| 666 | Right Carotid | 3.0 | P |
|  | Left Carotid | 2.5 | P |
|  | Left Carotid | 2.5 | — |
|  | Right Femoral | 3.2 | P |
| 668 | Right Carotid | 2.5 | P |
|  | Left Carotid | 2.5 | P |
|  | Right Femoral | 2.5 | P |
|  | Left Femoral | 2.0 | — |
|  | Left Axillary | 2.0 | — |
| 669 | Right Carotid | 3.5 | P |
|  | Left Carotid | 3.0 | P |
|  | Right Femoral | 3.5 | — |
| 702 | Right Carotid | 4.0 | O |
|  | Left Carotid | 3.0 | P |
|  | Right Femoral | 3.0 | P |
| 716 | Right Carotid | 3.5 | — |
|  | Left Carotid | 3.5 | — |
|  |  |  | No angio |

— Angiogram not carried out.
O Anastomosis not visualized on angiography.

Table 2 shows the results of in vivo end-to-end anastomosis in other dogs. Thirty three vascular anastomoses have been carried out in 11 dogs. Carotid, femoral and axillary vessels were used with diameters ranging from 1 to 3.5 mm. These animals have been followed for up to eight months following anastomosis (Table 2). The patency rates in the anastomoses that have had post-operative angiography have been 88%. Indeed, three of the four occlusions have been in brachial vessels which have been found unsuitable for anastomosis because of the excessive twisting of the graft in the axilla on movement of the limb of the dog when ambulating. If the brachial vessels are eliminated the patency rate is over 95%.

TABLE 2

| DOG NO. | VESSEL (artery) | DIAMETER (mm) | FOLLOW UP (months) | PATENCY (angio) |
|---|---|---|---|---|
| 741 | Right carotid | 3.0 | 3.0 | P |
|  | Left carotid | 3.5 | 1.5 | P |
|  | Right femoral | 3.0 | 2.0 | P |
| 740 | Right carotid | 3.5 | 3.0 | P |
|  | Left carotid | 3.0 | 2.5 | P |
|  | Right femoral | 1.0 | 3.0 | O |
| 739 | Right carotid | 3.0 | 1.5 | P |
|  | Left carotid | 3.0 | 2.0 | P |
|  | Right femoral | 2.5 | 2.0 | P |
| 726 | Right carotid | 3.5 | 6.0 | P |
|  | Left carotid | 3.5 | 4.0 | P |
|  | Right brachial | 2.5 | 6.0 | O |
|  | Left brachial | 2.5 | 6.0 | P |
|  | Right femoral | 3.5 | 6.0 | P |
|  | Renal | 3.0 | 4.0 | P |
| 718 | Right carotid | 3.5 | 1 week | P |
|  | Left carotid | 3.5 | 1 week | P |
| 717 | Right carotid | 3.0 | 3.0 | P |
|  | Left carotid | 3.0 | 3.0 | P |
|  | Right Brachial | 2.5 | 2.0 | P |
|  | Left Brachial | 2.5 | 2.5 | P |
|  | Right femoral | 3.0 | 3.0 | P |
| 716 | Left Brachial | 1.0 | 2.0 | P |
|  | Left femoral | 2.5 | 2.5 | P |
| 702 | Left brachial | 1.0 | 1.0 | P |
|  | Right brachial | 1.0 | 1.0 | P |
| 669 | Right brachial | 2.0 | 2.0 | P |
| 668 | Right brachial | 2.0 | 1.0 | P |
|  | Left brachial | 2.0 | 8.0 | P |
|  | Left femoral | 2.0 | 7.5 | P |
| 666 | Right brachial | 2.0 | 1.0 | P |
|  | Left brachial | 2.5 | 1.0 | O |
|  | Left carotid | 2.5 | 7.0 | P |

P: Patent
O: Occluded

End-to-Side

Assessment of graft patency, end-to-side.

In vitro experiments, using cadaver vessels, showed that the end-to-side device of the invention produced a functioning watertight anastomosis. Results with in vivo animal experiments have also been encouraging. Fourteen anastomoses were performed. In twelve procedures vein grafts were used between two arteries and end-to-side anastomosis performed at both ends. In two procedures single end-to-side anastomosis was done between two vessels. Thus a total of twenty six end to side prostheses were used in the preliminary assessment of the new method.

Further studies are continuing in the rabbit.

The rabbit's carotid artery has a diameter that ranges between 1.5 mm to 2 mm. Appropriate size clips were developed. To assess for graft patency both angiography and direct gross inspection of the anastomotic site has been carried out. A 100% patency rate has been achieved with the end-to-side anastomotic devices of the invention in those animals having had post-op assessment. This includes anastomoses in vessels ranging in size from 2 mm to 3.5 mm. Although these animals have to date been followed over only a few months, longer follow up studies will be carried out.

TABLE 3

| VESSEL (artery) | DIAMETER (mm) | PATENCY (angio) |
|---|---|---|

A. End-to-side anastomosis

| | | | |
|---|---|---|---|
| DOG No. | | | |
| 723 | Right brachial | 1.5 | P |
| 738 | Right brachial | 2.0 | NA |
|  | Left to right carotid | 3.0, 2.5 | NA |
| 739 | Right to left carotid | 3.0, 3.0 | P |
|  | Left brachial | 2.0 | P |
| 741 | Right to left carotid | 2.5, 3.0 | P |
|  | Right brachial | 2.0 | P |
| 740 | Right brachial | 1.5 | P |
|  | Left to right carotid | 3.5, 3.5 | P |
| 760 | Right to left carotid | 3.0, 3.0 | P |
|  | Left to right carotid | 3.0, 3.0 | P |
|  | Right brachial | 2.5 | P |
|  | Left brachial | 2.5 | P |
| RABBIT No. | | | |
| 339 | Right to left carotid | 2.0 | P |

B. End-to-end anastomosis

TABLE 3-continued

| | VESSEL (artery) | DIAMETER (mm) | PATENCY (angio) |
|---|---|---|---|
| RAT No. | | | |
| 295 | Carotid | 1.0 | P |
| 278 | Carotid | 1.0 | P |
| 247 | Carotid | 1.0 | P |
| 248 | Carotid | 1.0 | P |

P: Patent
O: Occluded
NA: Angio not done to date.

We claim:

1. An anastomosis kit for non-suture, non-adhesive connection of tubular tissue members to be anastomosed with overlapping intima to intima contact comprising:
a plurality of anastomosis devices, each device comprising:
a tubular connection member of sterilizable, biocompatible material having an inner cylindrical surface and an outer cylindrical surface,
first and second, spaced apart clip-retaining means on said outer surface, adjacent first and second ends of said connection member, respectively,
first and second clip members, each clip member having a ring-shaped body part and opposed ends separable under spring tension for temporary enlargement of the ring-shaped body part each body part defining a substantially circular opening, the body parts of said first and second clip members being adapted to circumferentially surround said outer cylindrical surface,
said opposed ends having opposed handling elements to facilitate handling of said clip members and separation of said opposed ends for temporary enlargement of the ring-shaped body parts and application of said clip members about tubular tissue applied over said outer surface of said tubular connection with essentially radial application of spring force on said tissue on release of force separating said opposed ends,
said devices being of different sizes in the diameter range of 0.75 mm to 7.5 mm,
a clip applicator comprising a pair of opposed legs connected at one end and having support means remote from said one end to supportingly engage the opposed handling elements of said clip members, said legs being operable under spring tension to separate said support means and the engaged opposed handling elements to enlarge said substantially circular opening; and
a holder for the connection members comprising a pair of opposed legs connected at one end and having opposed feet remote from said one end, adapted to engage the inner cylindrical surfaces of a connection member of said devices, said holder legs being operable under spring tension to forcefully urge said feet in opposite directions against opposed sides of the inner cylindrical surface of said connection member.

2. A kit according to claim 1, further including obturator means to measure the internal diameter of said tubular tissue members.

3. An anastomosis kit for non-suture connection of tubular tissue members comprising a plurality of devices, each device comprising:
a tubular connection member of sterilizable, biocompatible material having a smooth inner cylindrical surface, an outer cylindrical surface, and a clip-retaining means on said outer cylindrical surface adjacent a first end of said connection member,
tissue holding means on said connection member remote from said retaining means adapted to hold the end tissue material of a first vessel passed inwardly through said connection member and everted over said connection member from said first end,
clip means of sterilizable, biocompatible spring material having a ring-shaped body part defining a substantially circular opening, and opposed ends separable under spring pressure to enlarge said opening,
said ring-shaped body part being adapted to circumferentially surround said outer cylindrical surface,
a plurality of spaced apart tissue piercing and retaining members on said ring-shaped body part adapted to engage tissue material everted from a side opening in a second tissue member, and
said retaining means being effective to prevent axial dislodgement of the clip member mounted on said tubular member, at said first end,
said devices being of different sizes in the diameter range of 0.75 mm to 7.5 mm,
a clip applicator comprising a pair of opposed legs connected at one end and having support means remote from said one end to supportingly engage the opposed handling elements of said clip members,
said legs being operable under spring tension to separate said support means and the engaged opposed handling elements to enlarge said substantially circular opening, and
a holder for the connection member comprising a pair of opposed legs connected at one end and having opposed feet remote from said one end, adapted to engage the connection member of said devices, said holder legs being operable under spring tension to forcefully urge said feet in opposite directions against opposed sides of the connection member.

4. A kit according to claim 3, wherein said clip applicator further includes a stabilizing means adapted to supportingly engage said opposed handling elements.

5. A kit according to claim 4, further including obturator means to measure the internal diameter of said tubular tissue members.

* * * * *